United States Patent [19]

Larsen et al.

[11]  4,422,913
[45]  Dec. 27, 1983

[54] PROCESS FOR THE PRODUCTION OF 1,1,2-TRICHLORO-2,2-DIFLUOROETHANE

[75] Inventors: Eric R. Larsen; Ernest L. Ecker, both of Midland, Mich.

[73] Assignee: The Dow Chemical Company, Midland, Mich.

[21] Appl. No.: 324,184

[22] Filed: Nov. 23, 1981

[51] Int. Cl.$^3$ .................. B01J 19/12; C07C 17/04
[52] U.S. Cl. .................. 204/158 HA; 204/163 R; 570/123
[58] Field of Search .................. 204/158 HA, 163 R; 570/123, 252–255

[56] References Cited

U.S. PATENT DOCUMENTS 2,644,845  7/1953  McBee .................. 260/653
2,724,004  11/1955  Frederick .................. 260/653
4,324,930  4/1982  von Halasz .................. 204/158 HA

FOREIGN PATENT DOCUMENTS 523449  7/1940  United Kingdom.

OTHER PUBLICATIONS

McBee et al., "Fluorinated Derivatives of Ethane", vol. 39, No. 3, *Industrial & Engineering Chemistry* (1947), pp. 409–412.

Heberling, J. W. Jr., "Chlorination of 1,1-difluoro-2,2-dichloroethane" (1958), pp. 615–616.

*Primary Examiner*—Howard S. Williams
*Attorney, Agent, or Firm*—Paul D. Hayhurst

[57] ABSTRACT

The compound 1,1,2-trichloro-2,2-difluoroethane is prepared in high yield by contacting 1,1-difluoroethylene and chlorine in the presence of a free radical initiator in a liquid reaction medium.

15 Claims, No Drawings

PROCESS FOR THE PRODUCTION OF 1,1,2-TRICHLORO-2,2-DIFLUOROETHANE

BACKGROUND OF THE INVENTION

This invention relates to a new method for the preparation of 1,1,2-trichloro-2,2-difluoroethane.

The compound 1,1,2-trichloro-2,2-difluoroethane has been prepared in the past by a variety of methods. These methods include the thermal chlorination of $CClF_2CH_3$ and $CHF_2CH_3$, the reduction of $CClF_2CCl_3$ with isopropanol, and the fluorination of $CCl_3CHCl_2$ with antimony fluoride. Except for the fluorination of $CCl_3CHCl_2$ and the reduction of $CClF_2CCl_3$, 1,1,2-trichloro-2,2-difluoroethane was not the major product and yields were generally poor. The fluorination of $CCl_3CHCl_2$ suffers as a method of preparing 1,1,2-trichloro-2,2-difluoroethane because it involves corrosive HF and produces a hazardous, antimony-containing waste stream. The reduction of $CClF_2CCl_3$ is not a satisfactory method of making 1,1,2-trichloro-2,2-difluoroethane, due to the fact that $CClF_2CCl_3$ is simply 1,1,2-trichloro-2,2-difluoroethane which has been over-chlorinated.

In view of the deficiencies of the aforementioned known processes, it would be highly desirable to provide a process having a high selectivity to 1,1,2-trichloro-2,2-difluoroethane without having the problems associated with the methods of the prior art.

SUMMARY OF THE INVENTION

The present invention is such a highly selective process for producing 1,1,2-trichloro-2,2-difluoroethane. The process involves contacting 1,1-difluoroethylene with a chlorinating agent in the presence of a free radical initiator under conditions such that $CF_2ClCHCl_2$ is selectively obtained, said selectivity being greater than 63 mole percent based on 1,1-difluoroethylene. These selectivities are surprising in view of the results obtained by the techniques of the prior art.

The compound 1,1,2-trichloro-2,2-difluoroethane is a valuable intermediate for the preparation of highly desired chemicals. For example, 1,1,2-trichloro-2,2-difluoroethane may be combined with KOH and an alcohol to produce a halogenated ether via the method disclosed in British Patent Specification 523,449. Further, 1,1,2-trichloro-2,2-difluoroethane may be dehydrochlorinated to 1,1-dichloro-2,2-difluoroethylene, which in turn may be contacted with methanol in the presence of alkali to produce 2,2-dichloro-1,1-difluoroethyl methyl ether. See U.S. Pat. No. 3,264,356.

DETAILED DESCRIPTION OF THE INVENTION

In the practice of the present invention it is essential to employ 1,1-difluoroethylene, a chlorinating agent, and a free radical initiator. The compound 1,1-difluoroethylene is well-known, is commercially available, and can be prepared by a number of known methods.

A suitable halogen or any agent that is capable of generating chlorine atoms, such as a suitable chlorine-containing solid or liquid, can be used as the chlorinating agent. The preferred chlorinating agent is chlorine. Advantageously, the chlorinating agent is supplied in an amount such that an optimum amount of 1,1,2-trichloro-2,2-difluoroethane is produced. Typically, the molar feed ratio of $Cl_2$ to 1,1-difluoroethylene is from about 1.2 to about 2.5, preferably this ratio is from about 1.7 to 2.1. A lower or higher ratio may be employed, but low $Cl_2$/1,1-difluoroethylene molar feed ratios lead to excessive accumulation of $CF_2ClCH_2Cl$, while high ratios lead to accumulation of $CF_2ClCCl_3$ and a reduction in the selectivity of the process.

Suitable free radical initiators include catalysts, such as peroxides, and electromagnetic radiation. Electromagnetic radiation is the preferred free radical initiator. Any form of electromagnetic radiation which effects the instant chemical reaction may be employed, such as, for example, radiation in the visible and ultraviolet regions. Ultraviolet light is the most preferred free radical initiator. The output of the reaction system is a function of the light intensity, i.e., the rate of free radical formation, and the rate of addition of the reactants.

The chlorination of 1,1-difluoroethylene is advantageously conducted in a liquid reaction medium at a temperature which is between about $-20°$ C. and about $100°$ C. Preferably, the chlorination will be conducted between about $0°$ C. and about $40°$ C. Ordinarily, the reaction will proceed readily at atmospheric or higher pressure; subatmospheric pressures can be employed if desired. Preferably, the chlorination is conducted at atmospheric pressure.

The liquid reaction medium may be any suitable liquid which does not detract from the efficacy of the reaction. The liquid reaction medium contains a molar excess of $CF_2ClCH_2Cl$ with respect to $CF_2ClCHCl_2$, and the molar ratio of the former to the latter is typically 1.5 or greater. Preferably, the molar ratio of $CF_2ClCH_2Cl$ to $CF_2ClCHCl_2$ in the liquid reaction medium will be from about 2 to about 10. Most preferably, this ratio will be from about 3.5 to about 10. A ratio of 1.5 will result in a selectivity to 1,1,2-trichloro-2,2-difluoroethane of approximately 63 percent. Ratios which are greater than 10 result in excessive recycle of $CF_2ClCH_2Cl$ in exchange for a small small gain in selectivity. Preferably, a selectivity of 70 percent or more is obtained; most preferably a selectivity of 80 percent or greater is obtained. The term selectivity, when applied to the process of the present invention, means selectivity of 1,1,2-trichloro-2,2-difluoroethane, based on 1,1-difluoroethylene fed to the reaction vessel, and is calculated using the following equation:

Selectivity = $(100)(Y)/(Y+Z)$; wherein Y is moles of $CF_2ClCHCl_2$ in the product stream, and wherein Z is moles of $CF_2ClCCl_3$ in the product stream.

In a typical embodiment of the invention, the reaction vessel is charged with either $CF_2ClCH_2Cl$ or a mixture, from a previous run, of $CF_2ClCH_2Cl$, $CF_2ClCHCl_2$, and $CF_2ClCCl_3$. The reaction vessel contents are irradiated by free-radical-initiating electromagnetic radiation, and then gaseous chlorine and 1,1-difluoroethylene are fed simultaneously in separate feed streams having controlled flow rates to the reaction vessel through gas dispersion tubes. As the reaction proceeds, the liquid level rises in the reactor, gaseous HCl evolves from the liquid reaction medium, and the reactor is cooled in order to minimize vaporization of the relatively low boiling contents of the reactor, e.g., $CF_2ClCH_2Cl$ boils at about $47°$ C., said vaporization being promoted by the heat of the exothermic reaction and the thermal energy given off by typical lamps used to generate free-radical-initiating electromagnetic radiation.

Prior to the point in time at which the reactor will overflow into its overflow line, which is connected to a reboiler of a distillation column, said reboiler is charged with $CF_2ClCH_2Cl$ and heated to achieve a steady reflux. When the reactor overflows to the reboiler, the distillation column proceeds to separate the mixture in the reboiler. The temperature at the top of the distillation column is chosen so that the distillate is essentially pure $CF_2ClCH_2Cl$. A condenser at the top of the column condenses the vapors of the halogenated organic compounds. The condensate from the condenser is split into two streams; one for reflux to the distillation column and one as a recycle stream to the reactor.

The liquid in the reboiler becomes richer in 1,1,2-trichloro-2,2-difluoroethane and $CF_2ClCCl_3$ as the distillation progresses. This liquid may be withdrawn for purification, with a return of $CF_2ClCH_2Cl$ to the reboiler. Alternatively, when the amount of 1,1,2-trichloro-2,2-difluoroethane in the reboiler becomes sufficiently high, the chlorination may be halted and the distillation system can be used to purify the mixture. Then, after the purification is complete, the fraction rich in $CF_2ClCH_2Cl$ can be returned to the reboiler, the chlorination may be restarted, and the cycle can be repeated as desired.

The following example is given to illustrate the invention and should not be construed as limiting its scope. All percentages in the example are by weight unless otherwise indicated.

EXAMPLE 1

The process equipment includes:
(a) a 2.5 liter glass reaction vessel equipped with gas dispersion tubes at its lower end, bottom drain, and a cooling means;
(b) a one-liter, 3-necked glass vessel (reboiler) equipped with a bottom drain, a thermocouple, and a heating means;
(c) a 1"×18" glass distillation column packed with ¼" glass helices, and equipped with a thermocouple at its top and a vacuum jacket;
(d) a condensing means with an associated fraction-splitting means; and
(e) a 450 watt Hanovia ® medium pressure, quartz, mercury vapor lamp.

The process equipment is assembled so that the packed distillation column sits above the one-liter vessel. The condensing means with associated fraction-splitting means sits above the distillation column. The reaction vessel is placed so that any liquid overflow from it will flow by gravity to the one-liter vessel. The source of electromagnetic radiation is placed so that it will irradiate the contents of the reaction vessel.

The process is initiated by charging the one-liter vessel with 3.83 moles of $CF_2ClCH_2Cl$ and 0.13 moles of $CF_2ClCHCl_2$. The reaction vessel is charged with 20.5 moles of $CF_2ClCH_2Cl$, 3.41 moles of $CF_2ClCHCl_2$, and 0.35 moles of $CF_2ClCCl_3$. The one-liter vessel is heated so that a steady reflux is achieved through the distillation column. The lamp is placed approximately six inches away from the reaction vessel and is turned on.

At this point the gaseous reactants, chlorine and 1,1-difluoroethylene, are fed to the lower portion of the reaction vessel through the gas dispersion tubes. The molar feed ratio of $Cl_2$ to 1,1-difluoroethylene is 1.90. During a period of 29.35 hours 43.5 moles of $Cl_2$ and 22.9 moles of 1,1-difluoroethylene pass into the reaction vessel. During this same period, distillate from the one-liter vessel is passed into the reaction vessel at approximately 2.6 ml/min. The contents of the reaction vessel are clear, as opposed to being an undesirable yellow-green color which would indicate an excessive rate of chlorine addition.

The volume of liquid in the reaction vessel increases as the reaction progresses. The liquid overflows into the one-liter vessel through a line which contains a vapor seal. Gaseous HCl by-product is taken off the top of the reaction vessel and is routed to the condensing means. The energy being supplied to the one-liter vessel via the heating means causes the overflow liquid to be distilled. A portion of the distillate is returned from the condensing means to the distillation column and the remaining portion is forwarded to the reaction vessel. The temperature at the top of the distillation column is controlled at 45°–46° C. in order to provide a distillate which is greater than 95 mole percent $CF_2ClCH_2Cl$. This allows the liquid in the one-liter vessel to become enriched in 1,1,2-trichloro-2,2-difluoroethane and $CF_2ClCCl_3$.

The one-liter vessel is partially emptied whenever it becomes nearly full and the removed mixture is partially separated into its components. The fraction rich in $CF_2ClCH_2Cl$ is returned to the one-liter vessel. For the total period of the run, 5.30 moles of $CF_2ClCH_2Cl$ and 0.25 moles of $CF_2ClCHCl_2$ are returned to the one-liter vessel.

The total weight of all materials added to the system is 9.260 kg, of which 9.147 kg remain at the end of the run. The molar amounts, according to gas-liquid chromatographic analysis, of materials added to the system and recovered therefrom for the run are shown in Table I.

TABLE I

| Component | Mass Balance | |
|---|---|---|
|  | Moles In | Moles Out |
| $CF_2=CH_2$ | 22.9 | — |
| $Cl_2$ | 43.49 | — |
| $CF_2ClCCl_3$ | 0.35 | 2.35 |
| $CF_2ClCHCl_2$ | 3.8 | 17.6 |
| $CF_2ClCH_2Cl$ | 29.6 | 35.5 |
| HCl | — | 20.5 |
| Total Organic | 56.65 | 55.45 |

Organic recovery = mole percent.
Calculated Yield of 1,1,2-trichloro-2,2-difluoroethane = 82.8 mole percent based on $CF_2=CH_2$ fed.
Selectivity = 87.3 mole percent.
Conversion of $CF_2=CH_2$ = 100 percent.

What is claimed is:
1. A process comprising contacting 1,1-difluoroethylene with a chlorinating agent in the presence of a free radical initiator under conditions such that 1,1,2-trichloro-2,2-difluoroethane is obtained in greater than about 63 mole percent selectivity.

2. The process of claim 1 wherein the chlorinating agent is chlorine and the free radical initiator is electromagnetic radiation.

3. The process of claim 2 wherein the chlorine and 1,1-difluoroethylene are contacted in a liquid reaction medium.

4. The process of claim 3 wherein the liquid reaction medium comprises $CF_2ClCH_2Cl$ and $CF_2ClCHCl_2$ in a molar ratio which is at least 1.5 of the former to one of the latter, and wherein the molar feed ratio of chlorine to 1,1-difluoroethylene is from about 1.2 to about 2.5.

5. The process of claim 4 wherein the temperature of the liquid reaction medium is between about −20° C. and 100° C.

6. The process of claim 5 wherein the molar feed ratio of chlorine to 1,1-difluoroethylene is from about 1.7 to about 2.1, the temperature of the liquid reaction medium is from about 0° C. to about 40° C., the molar ratio of $CF_2ClCH_2Cl$ to $CF_2ClCHCl_2$ in the liquid reaction medium is from about 2 to about 10, and the free radical initiator is ultraviolet light.

7. The process of claim 1, 3 or 6 wherein the selectivity is at least 80 mole percent.

8. The process of claim 4 wherein the selectivity is at least 70 mole percent.

9. The process of claim 6 wherein the selectivity is at least 70 mole percent.

10. The process of claim 1 wherein the selectivity is at least 70 mole percent.

11. A process comprising contacting 1,1-difluoroethylene with chlorine in the presence of ultraviolet light at a temperature of from about −20° C. to about 100° C. in a liquid reaction medium comprising $CF_2ClCH_2Cl$ and $CF_2ClCHCl_2$ wherein the molar ratio of $CF_2ClCH_2Cl$ to $CF_2ClCHCl_2$ is at least about 1.5, thereby selectively producing 1,1,2-trichloro-2,2-difluoroethane.

12. The process of claim 11 wherein the molar feed ratio of chlorine to 1,1-difluoroethylene is from about 1.2 to about 2.5.

13. The process of claim 11 wherein the selectivity to $CF_2ClCHCl_2$ is at least about 63 mole percent.

14. The process of claim 11 wherein the selectivity to $CF_2ClCHCl_2$ is at least about 70 mole percent.

15. The process of claim 11 wherein the selectivity to $CF_2ClCHCl_2$ is at least about 80 mole percent.

* * * * *

UNITED STATES PATENT AND TRADEMARK OFFICE
CERTIFICATE OF CORRECTION

PATENT NO. : 4,422,913
DATED : December 27, 1983
INVENTOR(S) : Eric R. Larsen and Ernest L. Ecker It is certified that error appears in the above—identified patent and that said Letters Patent is hereby corrected as shown below:

Column 3, line 32, "lower end, bottom drain," should read -- lower end, a bottom drain, --.

Column 4, line 44, "Organic recovery = mole percent." should read -- Organic recovery = 98 mole percent. --.

Signed and Sealed this

Eighteenth Day of September 1984

[SEAL]

Attest:

GERALD J. MOSSINGHOFF

Attesting Officer    Commissioner of Patents and Trademarks